(12) United States Patent
Luo et al.

(10) Patent No.: US 11,319,519 B2
(45) Date of Patent: May 3, 2022

(54) METHOD AND APPARATUS FOR SCREENING COMPOUNDS THAT HAVE PREVENTATIVE AND THERAPEUTIC ACTIVITIES AGAINST ENDOTHELIAL GLYCOCALYX-RELATED DISEASES

(71) Applicants: MACAU GLCAO Biotechnology Research Center Limited, Macau (CN); Calroy Health Sciences, LLC, Scottsdale, AZ (US)

(72) Inventors: Yong Luo, Jiangsu (CN); Jinhua Wei, Jiangsu (CN); Zhou Wang, Jiangsu (CN); Ming Sun, Jiangsu (CN); Chen Chen, Scottsdale, AZ (US); Yuguang Du, Jiangsu (CN)

(73) Assignees: MACAU GLCAO Biotechnology Research Center Limited, Macau (CN); Calroy Health Sciences, LLC, Scottsdale, AZ (US)

( * ) Notice: Subject to any disclaimer, the term of this patent is extended or adjusted under 35 U.S.C. 154(b) by 171 days.

(21) Appl. No.: 16/712,724

(22) Filed: Dec. 12, 2019

(65) Prior Publication Data
US 2020/0199510 A1 Jun. 25, 2020

Related U.S. Application Data

(60) Provisional application No. 62/778,776, filed on Dec. 12, 2018.

(51) Int. Cl.
*C12M 3/06* (2006.01)
*C12M 1/12* (2006.01)
(Continued)

(52) U.S. Cl.
CPC ....... *C12M 23/16* (2013.01); *B01L 3/502715* (2013.01); *C12M 23/34* (2013.01);
(Continued)

(58) Field of Classification Search
CPC ...... C12M 23/16; C12M 23/34; C12M 25/14; C12M 25/02; C12M 41/48; C12M 41/00;
(Continued)

(56) References Cited

U.S. PATENT DOCUMENTS 7,725,267 B2 5/2010 Prabhakarpandian et al.
9,506,024 B2 11/2016 Marx et al.
(Continued)

FOREIGN PATENT DOCUMENTS

CN 101451105 B 6/2009
WO WO 2009/102751 A2 8/2009
(Continued)

OTHER PUBLICATIONS

Luther.; "Usage of a Microfluidic System to Investigate the Endothelial Glycoalyx in Vitro." Bachelor Thesis at the Biology, University of Bern; Jun. 2018; 37 Pages.
(Continued)

*Primary Examiner* — Michael L Hobbs
(74) *Attorney, Agent, or Firm* — Thorpe, North & Western

(57) ABSTRACT

The microfluidic chip can comprise at least one multichamber flow assembly that can comprise a plurality of microchannels. The plurality of microchannels can comprise a first microchannel that includes: a first inlet; a first outlet; and a first chamber fluidly connected to the first inlet and the first outlet. The plurality of microchannels can comprise a second microchannel that includes: a second inlet; a second outlet; and a second chamber fluidly connected to the second inlet and the second outlet. The multichamber flow assembly can comprise a porous biocompatible membrane oriented along a longitudinal interface between the first microchannel and the second microchannel, wherein the porous biocompatible membrane is permeable for movement of biomolecules from
(Continued)

the first chamber to the second chamber through the porous biocompatible membrane.

15 Claims, 13 Drawing Sheets

(51) Int. Cl.
    *C12N 5/077*     (2010.01)
    *B01L 3/00*     (2006.01)
    *C12M 1/00*     (2006.01)
    *C12N 5/071*     (2010.01)
    *C12M 1/36*     (2006.01)

(52) U.S. Cl.
    CPC ............ *C12M 25/14* (2013.01); *C12M 29/04* (2013.01); *C12N 5/069* (2013.01); *C12N 5/0661* (2013.01); *B01L 2300/0861* (2013.01); *C12M 41/48* (2013.01)

(58) Field of Classification Search
    CPC . C12N 5/0661; C12N 5/069; B01L 3/502715; B01L 2300/0861; G01N 33/5008; G01N 33/5014
    See application file for complete search history.

(56) References Cited

U.S. PATENT DOCUMENTS

| | | | |
|---|---|---|---|
| 9,725,687 | B2 | 8/2017 | Wikswo et al. |
| 10,012,640 | B2 | 7/2018 | Pant et al. |
| 2008/0017586 | A1* | 1/2008 | Matousek ................ B63J 4/004 210/739 |
| 2010/0240086 | A1* | 9/2010 | Kashanin ........... G01N 33/5029 435/29 |
| 2011/0256619 | A1 | 10/2011 | Vacanti et al. |
| 2013/0143230 | A1 | 6/2013 | Tolias et al. |
| 2015/0004077 | A1* | 1/2015 | Wikswo ................ C12M 35/08 422/502 |
| 2015/0361386 | A1* | 12/2015 | Liu ........................ C12M 25/02 435/297.1 |
| 2018/0320125 | A1 | 11/2018 | Levner et al. |

FOREIGN PATENT DOCUMENTS

| | | |
|---|---|---|
| WO | WO 2016/191332 A2 | 12/2016 |
| WO | WO 2018/017605 A1 | 1/2018 |

OTHER PUBLICATIONS

Martin et al.; "Excess sodium is deleterious on endothelial and glycocalyx barrier function: A microfluidic study." J Trauma Acute Care Surg; Wolters Kluwer Health, Inc.; Jul. 2018; vol. 85, Issue 1; pp. 128-134.

Tsvirkun et al.; "Microvasculature on a chip: study of the Endothelial Surface Layer and the flow structure of Red Blood Cells." Scientific Reports; Nature; Mar. 24, 2017; vol. 7, Article No. 45036; pp. 1-11.

* cited by examiner

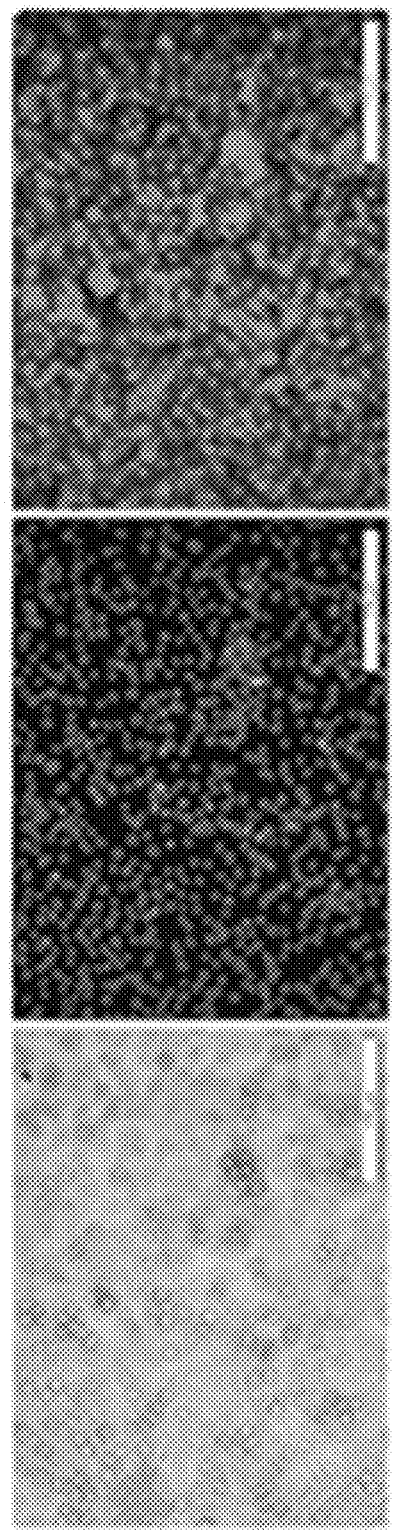
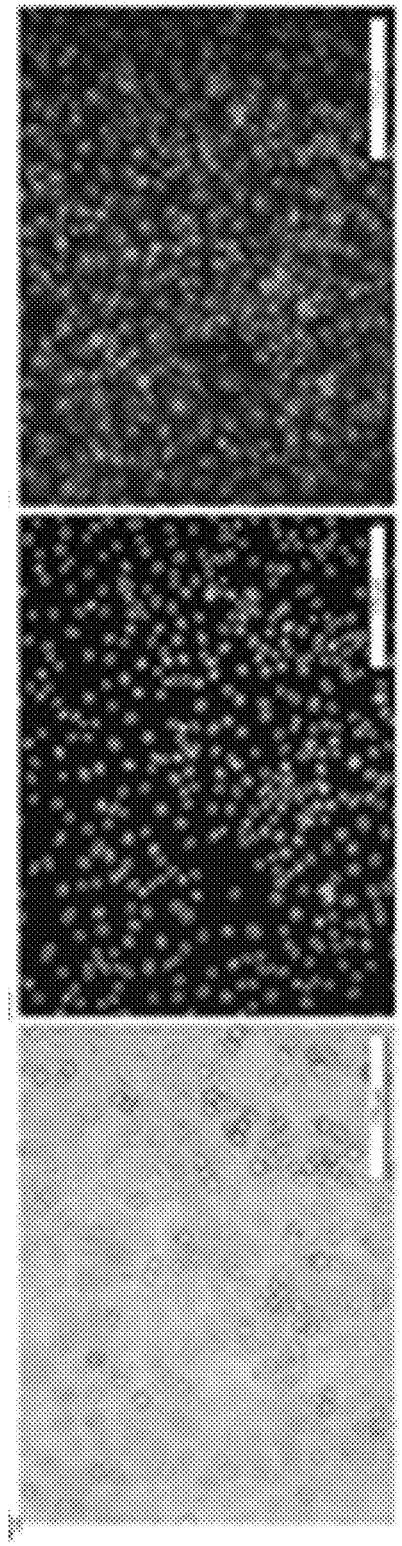

METHOD AND APPARATUS FOR SCREENING COMPOUNDS THAT HAVE PREVENTATIVE AND THERAPEUTIC ACTIVITIES AGAINST ENDOTHELIAL GLYCOCALYX-RELATED DISEASES

RELATED APPLICATION

This application claims priority to U.S. Provisional Application No. 62/778,776, filed Dec. 12, 2018, which is incorporated herein by reference in its entirety for all purposes.

BACKGROUND

Cardiovascular disease (CVS) is still the number one killer and, therefore, the biggest threat to human health in the world. One of the primary underlying causes of CVS is atherosclerosis. The hallmark of atherosclerosis is the development of atheroma or atheromatous plaques on the arterial walls resulting from an inflammatory response to endothelial injury. The latest research indicates that the damage of the endothelial glycocalyx is the earliest event in the pathogenesis of atherosclerosis.

The endothelial glycocalyx is a thin gel layer on the inner surface of all blood vessels including arteries, veins, and capillaries. The endothelial glycocalyx comprises proteoglycans, glycosaminoglycans, glycoproteins, and some docked serum proteins. The endothelial glycocalyx plays an important role and contributes to the maintenance of vascular homeostasis and health. The endothelial glycocalyx can regulate vascular permeability, maintain a normal vascular tone, provide a protective barrier for endothelium, inhibit cell adhesion and thrombosis, and mediate blood flow shear stress for signal transduction.

The endothelial glycocalyx is usually compromised in CVS, especially in the critically ill. The consequences include diminished or loss of the barrier function of the endothelial glycocalyx and increased endothelial permeability with abnormal water, electrolyte, and colloid balance. Low density lipoprotein (LDL) sticks to the endothelial cell surface and penetrates into subendothelial space. The damage of the endothelial glycocalyx also changes the adhesion and activity of some anticoagulant factors, thereby favoring thrombus formation. These changes increase the risk of the development of CVS and acute events associated with CVS. It can be recognized that maintaining the integrity of the endothelial glycocalyx can be an innovative approach to prevent and treat CVS.

SUMMARY

In one example, a microfluidic chip can comprise at least one multichamber flow assembly comprising a plurality of microchannels. The plurality of microchannels can comprise a first microchannel which includes: a first inlet; a first outlet; and a first chamber fluidly connected to the first inlet and the first outlet. The plurality of microchannels can comprise a second microchannel which includes: a second inlet; a second outlet; and a second chamber fluidly connected to the second inlet and the second outlet. The at least one multichamber flow assembly can comprise a porous biocompatible membrane oriented along a longitudinal interface between the first microchannel and the second microchannel. The porous biocompatible membrane is permeable for movement of biomolecules from the first chamber to the second chamber through the porous biocompatible membrane.

In one example, a method to grow endothelial cells with endothelial glycocalyx can use the microfluidic chip. The method can comprise seeding endothelial cells on the porous biocompatible membrane. The method can comprise growing the endothelial cells to 80% or greater confluence on a surface of the porous biocompatible membrane with a low flow rate of pumped cell culture medium in a $CO_2$ cell culture incubator. The method can comprise increasing the flow rate of cell culture medium to a high flow rate to mimic blood flow shear stress in vivo to increase growth of an endothelial glycocalyx on the endothelial cells. The method can comprise measuring at least one of a thickness and an integrity of the endothelial glycocalyx.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 8A-8F illustrates: human umbilical vein endothelial cells (HUVEC) morphology with a normal glucose level under a confocal microscope in accordance with an example (A); a nucleus with a normal glucose level under a confocal microscope in accordance with an example (B); glycocalyx with a normal glucose level under a confocal microscope in accordance with an example (C); HUVEC morphology with a high glucose level under a confocal microscope in accordance with an example (D); a nucleus with a high glucose level under a confocal microscope in accordance with an example (E); and glycocalyx with a high glucose level under a confocal microscope (F) in accordance with an example;

Figure 1:
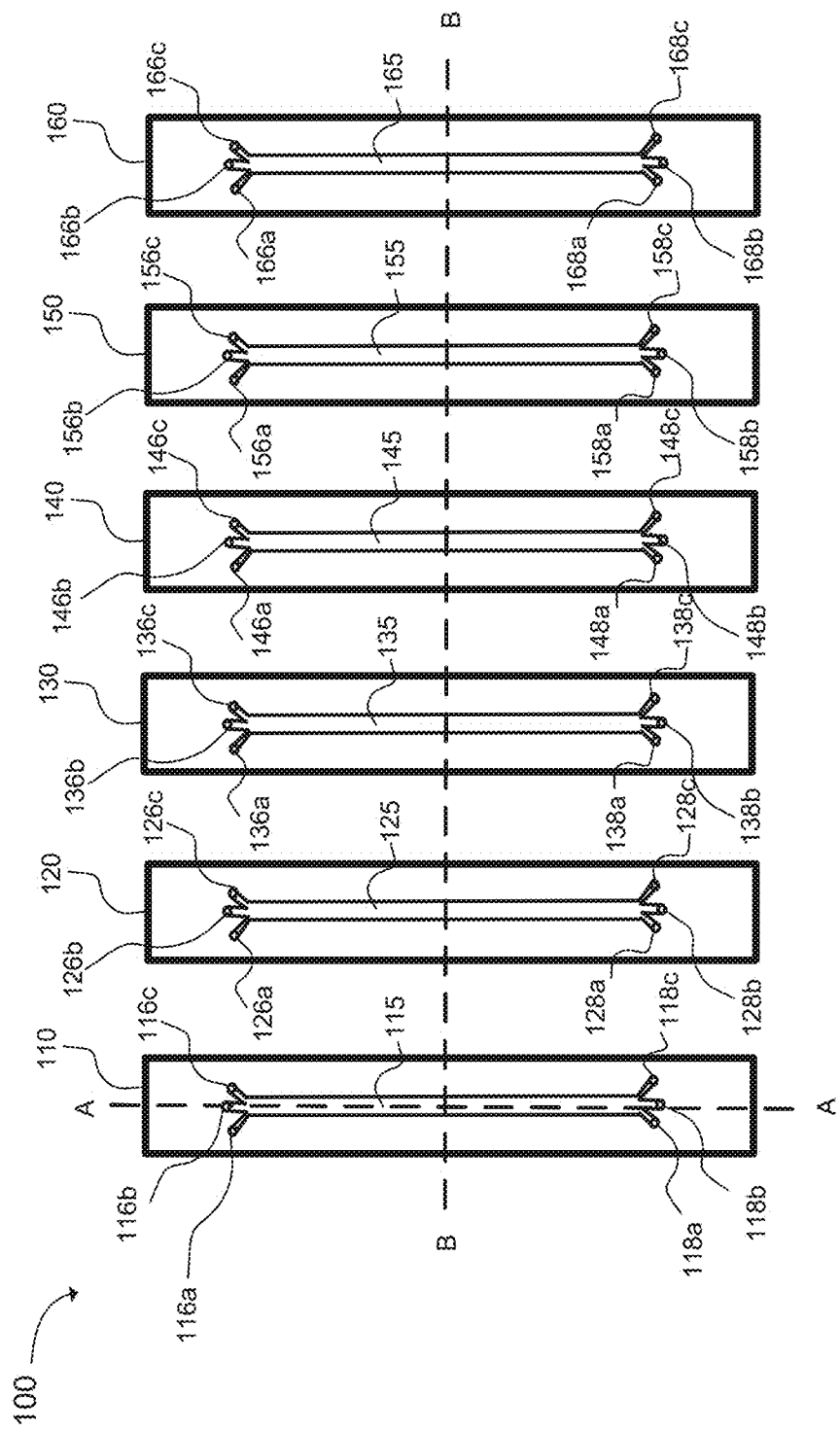
FIG. 1 ILLUSTRATES MICROARCHITECTURE OF A MICROFLUIDIC CHIP COMPRISING A MULTICHAMBER FLOW ASSEMBLY IN ACCORDANCE WITH AN EXAMPLE.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a particle" includes reference to one or more of such materials and reference to "flowing" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, "confluence" refers to the percentage of the surface of an interface of a cell-culture chamber that is covered by adherent cells. In one example, if the surface area of an interface of a cell-culture chamber is 10 square centimeters and about 8 square centimeters of the interface of the cell-culture chamber is covered by adherent cells, then the confluence of the cell-culture chamber is about 80%.

As used herein, "integrity" or "membrane integrity" refers to membrane integrity measured by a direct test or an indirect test. The membrane integrity measured by a direct test can refer to the extent of health or damage in the endothelial layer adhered to the membrane. The membrane integrity measured by an indirect test can refer to the amount of permeability of the membrane, length of glycocalyx, thickness (density), and/or total volume (e.g. via fluorescence spectroscopy).

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of" For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Method and Apparatus for Screening Compounds that have Preventive and Therapeutic Activities Against Endothelial Glycocalyx-Related Diseases An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

Research on the endothelial glycocalyx uses both in vivo and in vitro models. The in vivo research involves imaging of local endothelial glycocalyx integrity and also determination of total body endothelial glycocalyx volume. The results obtained by in vivo research technologies are believed to reflect the real conditions of the endothelial glycocalyx. However, the in vivo measurement of endothelial glycocalyx for research relies on sophisticated technologies to deal with complex biological environments at a high cost. The invasive nature of these sophisticated technologies can also make it difficult to obtain a large sample size for study.

On the other hand, in vitro cell culture can be simple and easy to perform in high volumes, large iterations, and across multiple laboratories. However, cell culture experiments are generally performed under static conditions and do not accurately mimic dynamic flow condition for normal growth of the endothelial glycocalyx. Thus, endothelial glycocalyx grown under in vitro cell culture conditions can be significantly different from the endothelial glycocalyx observed in vivo. This limitation can hinder endothelial glycocalyx research and the development of pharmaceutical products for CVS therapies.

In one example, microfluidic chip or lab-on-a-chip (LOC) can integrate various chemical and biological processes such as sample preparation, reaction, separation, detection, cell culture, cell manipulation, DNA purification, gene isolation, antigen-antibody interaction, drug delivery, biosensing, diagnosis, and the like at microchips of a centimeter scale that includes microchannels at micron levels. A microfluidic chip is a miniature platform that can be used to perform regular functions of chemical and biological laboratories through flow control. A microfluidic chip can include various properties such as a small scale, integrability, a high throughput, low energy consumption, and a reduced test time.

In another example, a microfluidic chip can possess some distinctive features for cell biology research. First, the size of the microchannels on the microfluidic chip (e.g., 10-100 micrometers (μm) in cross-section width) can be similar to the size of the microchannels of individual cells (e.g., 10-20 μm) to simplify cell manipulation. Second, the multi-dimensional network of microchannels on a microfluidic chip can provide a relatively isolated environment that can mimic the environment for living cells under normal physiological conditions. Third, a microfluidic chip can satisfy the demand of high throughput analysis by enabling the acquisition of a large volume of biological information in parallel. Fourth, the flat configuration of a microfluidic chip can allow for simple observation.

Therefore, a microfluidic chip can provide a useful in vitro platform model for mammalian cell culture and manipulation because it can simulate physiological conditions for experiments. However, using a microfluidic chip to simulate the changes in the endothelial glycocalyx and the resulting functional variations of vascular endothelium is lacking. A miniaturized research platform that can mimic physiological conditions can be valuable for: (a) studying endothelial glycocalyx-mediated pathogenesis, and (b) screening endothelial glycocalyx protecting and regenerating compounds (eGPRC) for therapeutic purposes.

In one example, a microfluidic chip can include at least one multichamber flow assembly comprising a plurality of microchannels. The plurality of microchannels can comprise a first microchannel can include: a first inlet; a first outlet; and a first chamber fluidly connected to the first inlet and the first outlet. The plurality of microchannels can comprise a second microchannel which includes: a second inlet; a second outlet; and a second chamber fluidly connected to the second inlet and the second outlet. The multichamber flow assembly can comprise a porous biocompatible membrane oriented along a longitudinal interface between the first microchannel and the second microchannel, wherein the porous biocompatible membrane is permeable for movement of biomolecules from the first chamber to the second chamber through the porous biocompatible membrane. In some cases, biomolecules can further also move from the second chamber to the first chamber based on porosity and relative concentration gradients or diffusion driving factors (i.e. osmotic pressure, temperature gradients, flow rate, etc).

In one example, a microfluidic chip can be fabricated to culture endothelial cells that form a healthy layer of the endothelial glycocalyx. The method can comprise using the fabricated chip as a model to measure the dynamic changes and related biological functions of the endothelial glycocalyx under different pathophysiological conditions. The model can be configured to adequately simulate endothelial cell validity and endothelial permeation. The model can be configured to screen pharmacologically active compounds to protect and regenerate endothelial glycocalyx (eGPRC).

Figure 2:
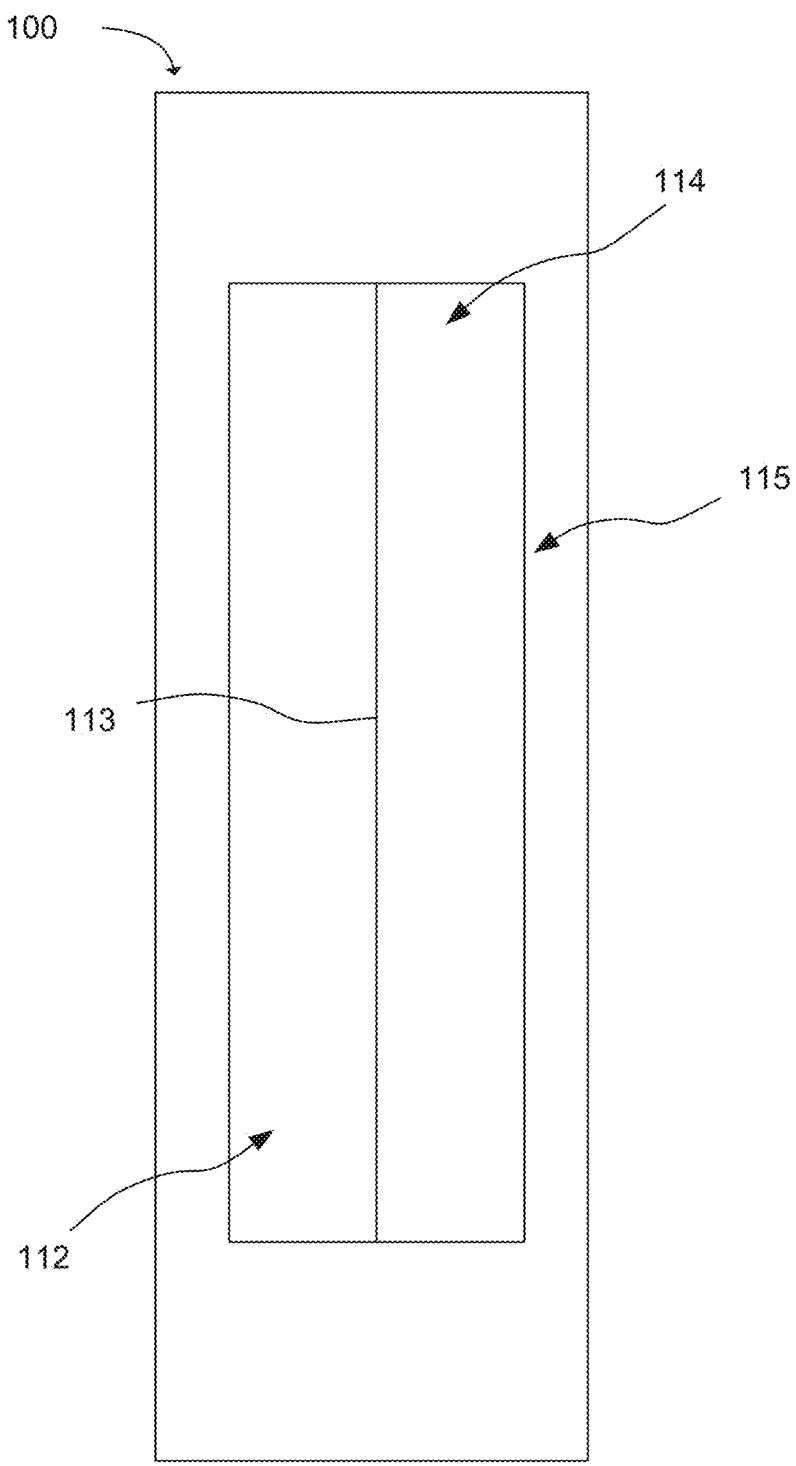
FIG. 2 illustrates a side cross-sectional view along A-A of the microfluidic chip comprising a multichamber flow assembly in accordance with FIG. 1.
Figure 3:
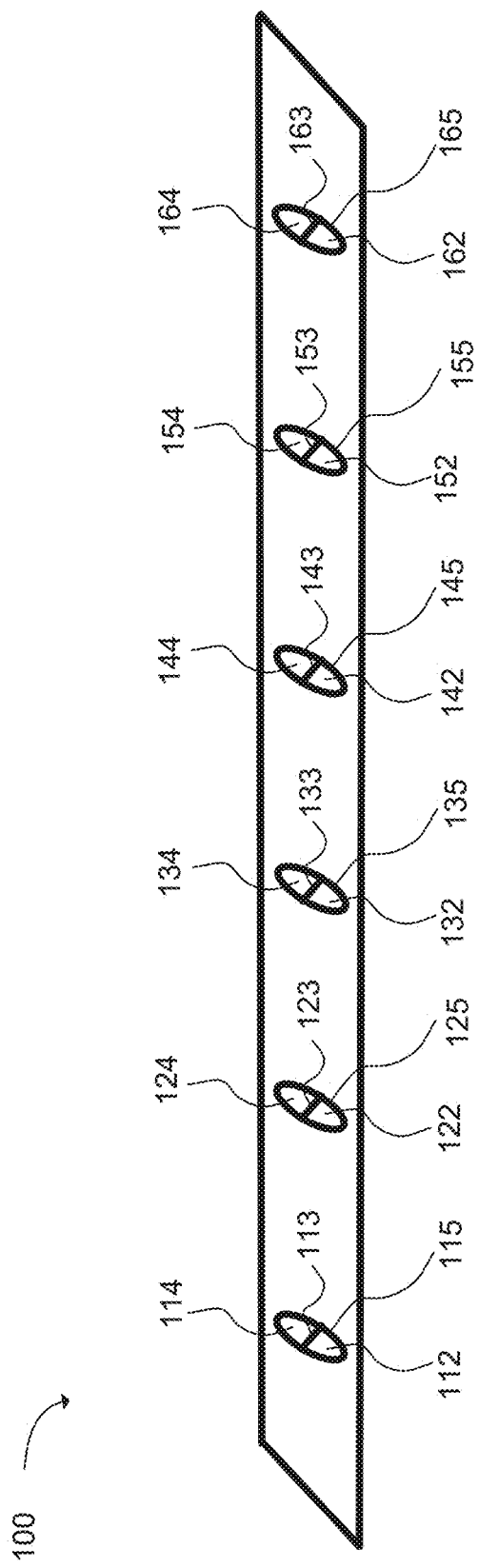
FIG. 3 illustrates side cross-sectional view along B-B of the microfluidic chip comprising a multichamber flow assembly in accordance with FIG. 1.

In one example, as illustrated in FIG. 1, a microfluidic chip 100 can include at least one multichamber flow assembly (e.g., 110, 120, 130, 140, 150, and 160). Each multichamber flow assembly 110, 120, 130, 140, 150, and 160 can include a plurality of microchannels (e.g., 115, 125, 135, 145, 155, and 165) and a porous biocompatible membrane (e.g., See FIGS. 2 and 3 features 113, 123, 133, 143, 153, and 163). The plurality of microchannels can each include parallel cell culture chambers (e.g., 112 and 114; 122 and 124; 132 and 134; 142 and 144; 152 and 154; and 162 and 164 as shown in FIG. 3) can each have at least one inlet (116a-c, 126a-c, 136a-c, 146a-c, 156a-c, and 166a-c), at least one cell culture chamber (e.g., 112 and 114; 122 and 124; 132 and 134; 142 and 144; 152 and 154; and 162 and 164), and at least one outlet (118a-c, 128a-c, 138a-c, 148a-c, 158a-c, and 168a-c).

In another example, the cell culture chambers 112 and 114 are fluidly connected to the inlets (116a, 116b, and 116c) on an inlet end and the outlets (118a, 118b, and 118c) on an outlet end. As illustrated in FIG. 2, the porous biocompatible membrane 113 can be oriented along a longitudinal interface between at least two cell culture chambers (e.g., 112 and 114 in multichamber flow assembly 110) of the plurality of microchannels, wherein the porous biocompatible membrane 113 can be permeable to allow the movement of biomolecules between the at least two cell culture chambers (e.g., 112 and 114 in multichamber flow assembly 110) through the porous biocompatible membrane 113. When cells cover the porous biocompatible membrane 113 at 100% confluence, the passage of liquid or bio-components can be controlled by the cell layer. Although device configurations can vary, channel width can generally range from about 100 µm to 2 cm, and most often from about 800 µm to 1 cm. Similarly, channel lengths can vary from about 0.5 cm to about 30 cm, and often about 1 cm to 10 cm.

In another example, the microfluidic chip 100 can have a layer-by-layer architecture including a plurality of slabs (e.g., a top slab of cell culture chamber 114 and a bottom slab of cell culture chamber 112). The plurality of microchannels can be formed from a top slab of cell culture 114 and a bottom slab of cell culture 112 for multichamber flow assembly 110. The complementary slabs of cell culture chambers 112 and 114 can form the plurality of microchannels.

In another example, although a variety of materials can be used for the complementary slabs of cell culture chambers 112 and 114, the material for the complementary slabs of cell culture chambers 112 and 114 can be transparent (e.g. transparent air permeable polydimethylsiloxane (PDMS)) to allow for optical interrogation of the culture chambers 112 and 114. However, any biocompatible materials can be used as long as the structural integrity of the microchannels can be maintained. Non-limiting examples of biocompatible materials can include polycarbonate, polymethyl methacrylate (PMMA), polyacrylamide (PAAM), hydrogels, and the like.

In another example, the top slab of cell culture chamber 114 and bottom slab of cell culture chamber 112 can be sealed together with the porous biocompatible membrane 113 in between and separating the two cell culture chambers 112 and 114. The seal can be a reversible seal with a removable assembly allowing for cleaning or reuse. The seal can also be irreversible, e.g. for single or limited use. Sealing can be performed using various bonding methods including but not limited to at least one of partial curing, varying curing ratio, uncured PDMS adhesive, oxygen plasma, and corona discharge.

In another example, the porous biocompatible membrane 113 can be formed of any suitable porous material that is biocompatible. In one example, the porous biocompatible membrane 113 can be comprised of at least one of polycarbonate, collagen treated polytetrafluoroethylene (PTFE), polyesters, and the like. The porous biocompatible membrane can include pores with a diameter ranging from at 0.1 to 10 µm. In another example, the porous biocompatible membrane can include pores with a diameter ranging from 0.2 to 1.0 µm. Although membrane interface area can be varied to accommodate a desired culture volume, practical surface area tends to range from 0.005 to 60 $cm^2$, and most often 0.08 to 10 $cm^2$. Thickness of the membrane can also vary based on the materials and desired porosity. However, as a general guideline, membrane thicknesses can range from about 10 µm to about 1 mm, and most often 50 µm to about 500 µm.

Referring again to FIG. 1, at least one multichamber flow assembly 110, 120, 130, 140, 150, and 160 can comprise a dedicated seeding inlet (e.g., 116b, 126b, 136b, 146b, 156b, or 166b) and a dedicated seeding outlet (e.g., 118b, 128b, 138b, 148b, 158b, or 168b). For example, a seeding inlet 116b and a seeding outlet 118b can be provided in at least one of the cell culture chambers 112 or 114 and oriented at the inlet end 116b and outlet end 118b.

In another example, although a single multichamber flow assembly 110 can be used, acquisition of multiple datapoints, increasing throughput, and allowing testing of multiple candidate materials can be desirable. Accordingly, more than one multi-chamber flow assembly 110, 120, 140, 150, and 160 can be integrated onto each microfluidic chip 100. The number of multichamber flow assemblies on a common microfluidic chip 100 (i.e. substrate) is not physically limited; however, can often range from one to three, and in some cases at least two flow assemblies. In another example, multiple multichamber flow assemblies can be provided by connecting multiple microfluidic chips together such that multiple substrates each having one or more flow assemblies can be connected to form a larger composite device.

In another example, the microfluidic chip 100 can comprise a plurality of multichamber flow assemblies 110, 120, 130, 140, 150, and 160 with a plurality of microchannels 115. A first multichamber flow assembly 110 can comprise three inlets 116a, 116b, and 116c and three outlets 118a, 118b, and 118c. The first multichamber flow assembly 110 can comprise a bottom cell culture chamber 112 and a top cell culture chamber 114 separated by an interface 113 comprising a porous biocompatible membrane 113.

In another example, a second multichamber flow assembly 120 can comprise three inlets 126a, 126b, and 126c and three outlets 128a, 128b, and 128c. The first multichamber flow assembly 120 can comprise a bottom cell culture chamber 122 and a top cell culture chamber 124 separated by an interface 123 comprising a porous biocompatible membrane 123 in a plurality of microchannels 125.

In another example, a third multichamber flow assembly 130 can comprise three inlets 136a, 136b, and 136c and three outlets 138a, 138b, and 138c. The third multichamber flow assembly 130 can comprise a bottom cell culture chamber 132 and a top cell culture chamber 134 separated by an interface 133 comprising a porous biocompatible membrane 133 in a plurality of microchannels 135.

In another example, a fourth multichamber flow assembly 140 can comprise three inlets 146a, 146b, and 146c and three outlets 148a, 148b, and 148c. The fourth multichamber flow assembly 140 can comprise a bottom cell culture chamber 142 and a top cell culture chamber 144 separated by an interface 143 comprising a porous biocompatible membrane 143 in a plurality of microchannels 145.

In another example, a fifth multichamber flow assembly 150 can comprise three inlets 156a, 156b, and 156c and three outlets 158a, 158b, and 158c. The fifth multichamber flow assembly 150 can comprise a bottom cell culture chamber 152 and a top cell culture chamber 154 separated by an interface 153 comprising a porous biocompatible membrane 153 in a plurality of microchannels 155.

In another example, a sixth multichamber flow assembly 160 can comprise three inlets 166a, 166b, and 166c and three outlets 168a, 168b, and 168c. The sixth multichamber flow assembly 160 can comprise a bottom cell culture chamber 162 and a top cell culture chamber 164 separated by an interface 163 comprising a porous biocompatible membrane 163 in a plurality of microchannels 165.

Referring to FIG. 3, the porous membrane (113, 123, 133, 143, 153, 163) can be seeded with various types of endothelial cells including, but not limited to, human umbilical endothelial cells (HUVECs), human arterial endothelial cells (HAECs), bovine aortic endothelial cells (BAECs), pulmonary microvascular endothelial cells (PMVECs), pulmonary artery endothelial cells (PAECs), human dermal microvascular endothelial cells (HDMECs), and the like adhered to the porous biocompatible membrane (113, 123, 133, 143, 153, 163). Cells can be seeded and adhered to a single side of the membrane 113, 123, 133, 143, 153, 163 (e.g., top side or bottom side) or both sides of the membrane (e.g., top and bottom sides). In some cases, opposing sides of the membrane can be seeded with different cell types.

In another example, a pump can be fluidly connected to the inlets (e.g., 116a-c, 126a-c, 136a-c, 146a-c, 156a-c, and 166a-c) and the outlets (118a-c, 128a-c, 138a-c, 148a-c, 158a-c, and 168a-c) to circulate a cell culture medium through at least one of the plurality of microchannels (e.g., 112, 114, 122, 124, 132, 134, 142, 144, 152, 154, 162, and 164). The pump can maintain a substantially continuous flow across the endothelial cells which mimics biological conditions.

Figure 4:
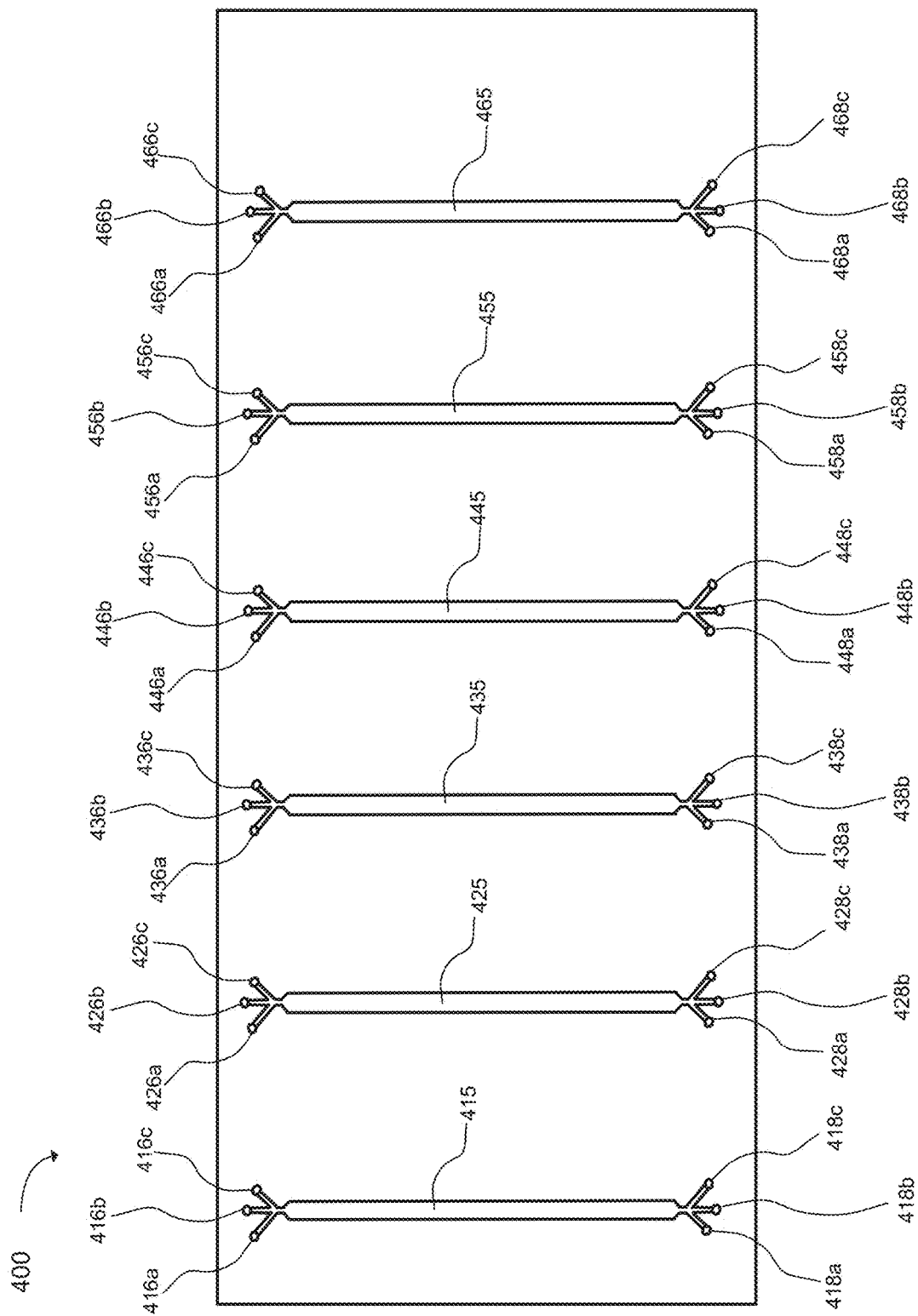
FIG. 4 illustrates microarchitecture of a microfluidic chip comprising a multichamber flow assembly in accordance with an example.

In another example, as illustrated in FIG. 4, a cross-section of a microfluidic chip 400 can comprise: a first multichamber flow assembly 415, a second multichamber flow assembly 425, a third multichamber flow assembly 435, a fourth multichamber flow assembly 445, a fifth multichamber flow assembly 455, and a sixth multichamber flow assembly 465. In this case, the inlet and outlet regions have a channel cross-section area which is smaller than a cross-sectional area of the primary channel (i.e. combined areas of each of the cell-culture chambers).

As with FIG. 1, each of the multichamber flow assemblies of FIG. 4 can include a first cell-culture chamber and a second cell-culture chamber separated by a porous biocompatible membrane. Further, the microfluidic chip 400 can comprise a plurality of multichamber flow assemblies. A first multichamber flow assembly can comprise three inlets 416a, 416b, and 416c and three outlets 418a, 418b, and 418c. A second multichamber flow assembly can comprise three inlets 426a, 426b, and 426c and three outlets 428a, 428b, and 428c. The third multichamber flow assembly can comprise three inlets 436a, 436b, and 436c and three outlets 438a, 438b, and 438c. The fourth multichamber flow assembly can comprise three inlets 446a, 446b, and 446c and three outlets 448a, 448b, and 448c. The fifth multichamber flow assembly can comprise three inlets 456a, 456b, and 456c and three outlets 458a, 458b, and 458c. The sixth multichamber flow assembly can comprise three inlets 466a, 466b, and 466c and three outlets 468a, 468b, and 468c.

Figure 5:
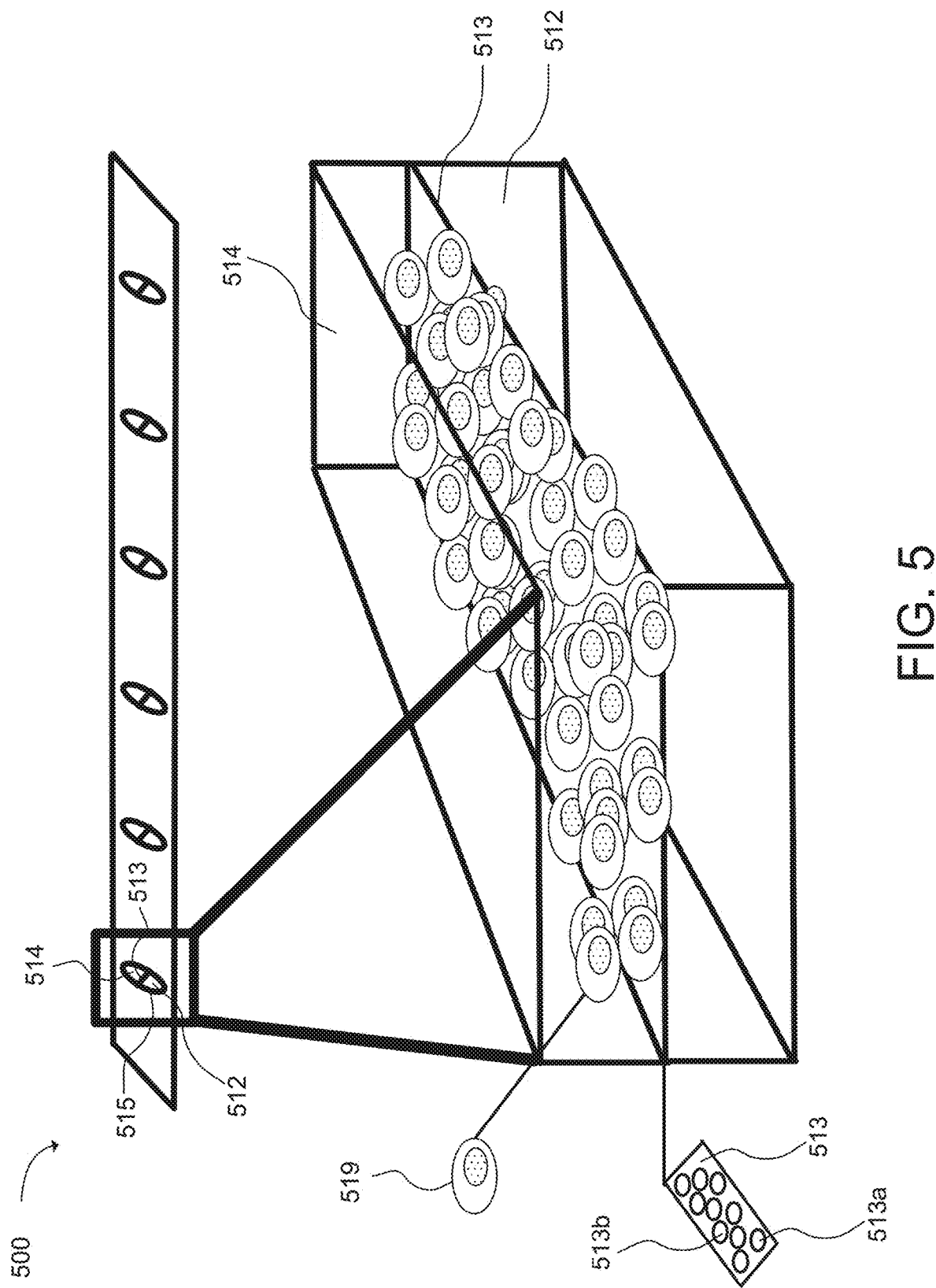
FIG. 5 illustrates microarchitecture of a microfluidic chip comprising a multichamber flow assembly including endothelial cells in accordance with an example.

As another perspective, as illustrated in FIG. 5, a cross-section of a microfluidic chip 500 can include a plurality of microchannels 515 with a first layer 512, a second layer 514, and an interface 513 separating the first layer 512 from the second layer 514 along a longitudinal interface 513. The interface 513 can include a plurality of endothelial cells (e.g., 519) on a top of the interface 513 or a bottom of the interface 513, or on both sides of the interface. The interface 513 can be a porous biocompatible membrane 513 with a plurality of pores (e.g., 513a, 513b, and the like).

A method to grow endothelial cells with healthy endothelial glycocalyx can include using any of the microfluidic chips described herein. In one example, microfluidic chip 500 can be used by seeding endothelial cells 519 on the porous biocompatible membrane 513. The endothelial cells 519 can be grown to at least 80% confluence on a surface of the porous biocompatible membrane 513 with a low flow rate of pumped culture medium. In some cases, growth can produce at least 90%, and in some cases about 100% confluence. In some cases, the growth stage can be performed in a $CO_2$ cell culture incubator. For example, the chamber can have a $CO_2$ control system which monitors and adjusts $CO_2$ levels within the chamber. Subsequent to growth, the flow rate of culture medium can be accelerated to a high flow rate to mimic blood flow shear stress in vivo for growth and maintenance of an endothelial glycocalyx on the endothelial cells 519. A thickness and integrity of the endothelial glycocalyx can be measured by fluorescence intensity of wheat germ agglutinin (WGA) fluorescein isothiocyanate conjugate (FITC) (WGA-FITC) bound to the glycocalyx.

In another example, seeding can produce a cell density ranging from $1-9 \times 10^4$-$1-9 \times 10^6$ cells/milliliter (ml) in the seeding medium. Although other flow rates can be suitable, the low flow rate can range between 1-60 µl/minute. In another example, the high flow rate can be sufficient to mimic blood flow and pressures. In one example, the high flow rate can range between 250-300 µl/min for a 16 mm×10 mm×0.1 mm chamber. In one example, the flow velocity can be selected to achieve a cell shear stress at cell surfaces ranging between 10-23 dyne (dyn)/squared centimeters ($cm^2$).

In another example, the plurality of microchannels can be perfused with a common cell culture medium at medium flow rates ranging between 60-250 µl/min. FITC-DEXTRANS can be inserted into the plurality of microchannels for a certain period of time. A fluorescence intensity can be measured in the lower channels to calculate a permeation rate (Papp (cm/s)) of each dextran. The thickness and integrity of the endothelial glycocalyx can be measured based on a permeation rate of a FITC-DEXTRANS.

In another example, various measurement methods can be used to measure the integrity of the endothelial glycocalyx. WGA-FITC is a direct method of measuring the integrity of the endothelial glycocalyx because WGA-FITC can bind to polysaccharides in the glycocalyx, and can be used to determine the length, thickness (density), and/or total volume of the glycocalyx based on 3-D fluorescent intensity. However, FITC-Dextrans is an indirect method of measuring the integrity of the glycocalyx because FITC-Dextrans can pass through the glycocalyx to allows for measurement of the thickness of the glycocalyx but not the length of the glycocalyx based on the permeability of the sizes of FITC-Dextrans.

In another example, in order to mimic specific conditions, the method can include adding a level of glucose into the cell culture medium and maintaining a high flow rate to mimic a diabetic hyperglycemic condition to produce a stressed glycocalyx. Subsequently, a stressed thickness and stressed integrity of the endothelial glycocalyx can be measured. Specific glucose conditions can be varied, but in one case the glucose can be introduced at a concentration ranging between 25-75 millimolar (mM) and the high flow rate can be maintained for a period of time ranging between 24-72 hours.

In another example, various concentrations of different test compounds can be introduced into the cell culture medium. Subsequent to maintaining flow of such test compounds through the cell chamber for a given period of time, the effects on the endothelial glycocalyx can be measured. For example, a test permeation rate can be measured to calculate a test thickness and a test integrity of the endothelial glycocalyx in order to measure a protective impact and/or damage to the endothelial glycocalyx. This approach can be used for screening candidate treatment compounds.

In another example, the permeation rates of different sizes of Dextrans can be calculated and compared to those of blank, a negative control, and a positive control based on the fluorescence intensities in the lower microchannels. Based on the changes of the specific permeation rate, each compound introduced into the upper microchannels can be evaluated for its effectiveness in protecting the endothelial glycocalyx.

In another example, a method to screen pharmacologically active compounds for regenerating and restoring the endothelial glycocalyx can also include perfusing microchannels (e.g., cell culture chambers) with a different cell culture medium with various concentrations of different compounds but no additional glucose after HUVECs are incubated under hyperglycemic condition for 24-72 hours. As with other examples, the permeation rates of different Dextrans can be calculated and compared to those of a blank, a negative control, and a positive control based on the fluorescence intensities in the lower microchannels. Based on changes in the specific permeation rate, each compound introduced into the upper microchannels can be evaluated for their effectiveness in regenerating and restoring the endothelial glycocalyx.

In another example, white blood cells can be introduced into the cell culture to allow contact with the endothelial surface. The number of white blood cells patrolling on and adhering to endothelial cell layer can be visualized and determined using a confocal microscope.

In another example, the patrolling velocity of white blood cells can be determined. Damage to the endothelial glycocalyx can increase cell adhesion and decrease cell rolling as a response to glycocalyx-mediated endothelial inflammation. Penetration of white blood cells through endothelial cell layer can also occur in diapedesis.

In another example, smooth muscle cells can be grown in the second chamber. Changes in RNA expression, DNA expression, or protein synthesis of the smooth muscle cells can be determined using the microfluidic chip.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

EXAMPLES

Example 1: Design of a Layer-by-Layer Microfluidic Chip

In one example, the microfluidic chip can have a layer-by-layer architecture. Both the top lawyer and the bottom layer can be comprised of transparent and gas permeable polydimethylsiloxane (PDMS). Two microchannel slabs can be reversibly sealed with a porous biocompatible membrane in between that separates the two cell culture chambers. The porous membrane can be made of any biocompatible material such as polycarbonate and the sizes of pores can include a range between 0.1-10 micrometers (μm).

In another example, as previously discussed with reference to FIGS. 1-5, at least six multichamber flow assemblies (e.g., 110, 120, 130, 140, 150, and 160) can be casted in a microfluidic chip (e.g., 100). Each multichamber flow assembly (e.g., 110) can include: 3 inlets (e.g., 116a, 116b, and 116c); 2 cell culture chambers (top microchannels 114 and bottom microchannels 112); and 3 outlets (e.g., 118a, 118b, and 118c), although the number inlets and the number of outlets can vary. The cell culture chambers (112 and 114) can be connected to inlets (e.g., 116a, 116b, and 116c) on one side and outlets (118a, 118b, and 118c) on the other side. The left inlet (e.g., 116a) and outlet (e.g., 118a) can be connected to the top cell culture chamber 114. The right inlet (e.g., 116c) and outlet (e.g., 118c) can be connected to the bottom cell culture chamber 112. The middle inlet (e.g., 116b) and outlets (e.g., 118b) can be connected to the top chamber 114 to deliver endothelial cells onto the porous biocompatible membrane 113 for seeding under the static condition. In this example, flow through each of the top 114 and bottom 112 chambers can be controlled through valves or other flow control mechanisms fluidly associated with the inlets (e.g., 116a, 116b, and 116c) and outlets (e.g., 118a, 118b, and 118c).

Example 2: Seeding and Culture of Endothelial Cells Inside Chip

In one example, a method of seeding and culturing endothelial cells can include digesting human umbilical vein endothelial cells (HUVECs) with a pipette and adjusting the cell density to a proper level (e.g., $1\text{-}9\times10^4\text{-}1\text{-}9\times10^6$ cells/milliliter (ml)). The method of seeding and culturing endothelial cells can further include delivering HUVECs to the upper cell culture chambers 114 with porous biologically compatible membranes 113 inside the chip through middle inlet (e.g., 116b) and moving the chip inside a $CO_2$ cell culture incubator. The method of seeding and culturing endothelial cells can further include incubation for 4-6 hours, connecting the chip inlets (e.g., 116a and 116c) and outlets (e.g., 118a and 118c) to pumped cell culture media, and growing the cells to 80% confluency with a low flow rate (e.g., 1-60 μl/min). The method of seeding and culturing endothelial cells can further include increasing the cell culture media flow rate to simulate the high shear stress of blood flow (e.g., 250-300 μl/min in this case). The flow rates can vary based on the size of the channels and the desired high shear conditions). The lower cell culture chambers 112 can be closed until the introduction of the high flow rate in the upper chamber 114 and can be perfused with the same cell culture medium at the same high flow rate.

Figures 6A, 6B:
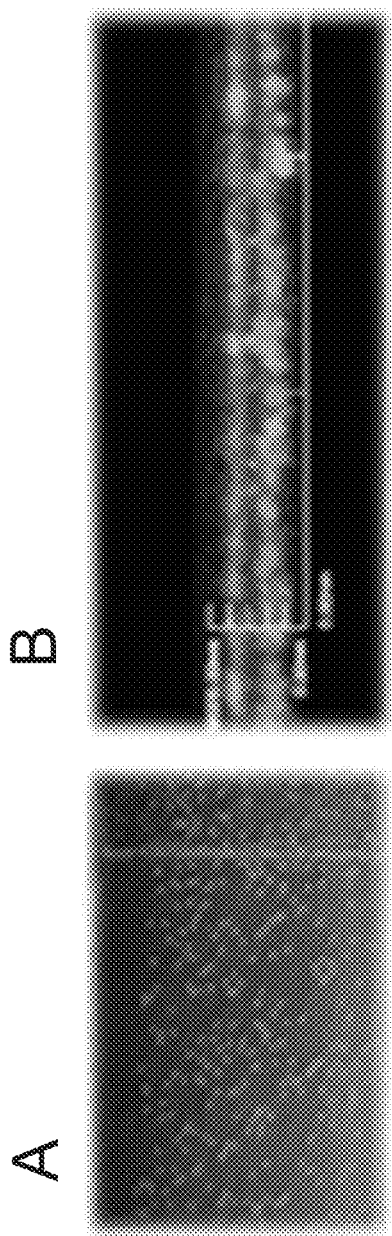
FIGS. 6A and 6B illustrates: human umbilical vein endothelial cells (HUVEC) morphology under a normal confocal microscope (A) in accordance with an example; and a fluorescence stain of endothelial cell nucleus (blue) and glycocalyx (green) (B) in accordance with an example.

In another example, two methods can be used to evaluate the glycocalyx condition on the surface of a confluent endothelial cell layer. One method can include using Wheat Germ Agglutinin Fluorescein Isothiocyanate Conjugate (WGA-FITC) to bind and measure the length and thickness of the glycocalyx gel layer via 3-dimensional fluorescence strengths, as illustrated in FIG. 6.

Figure 7:
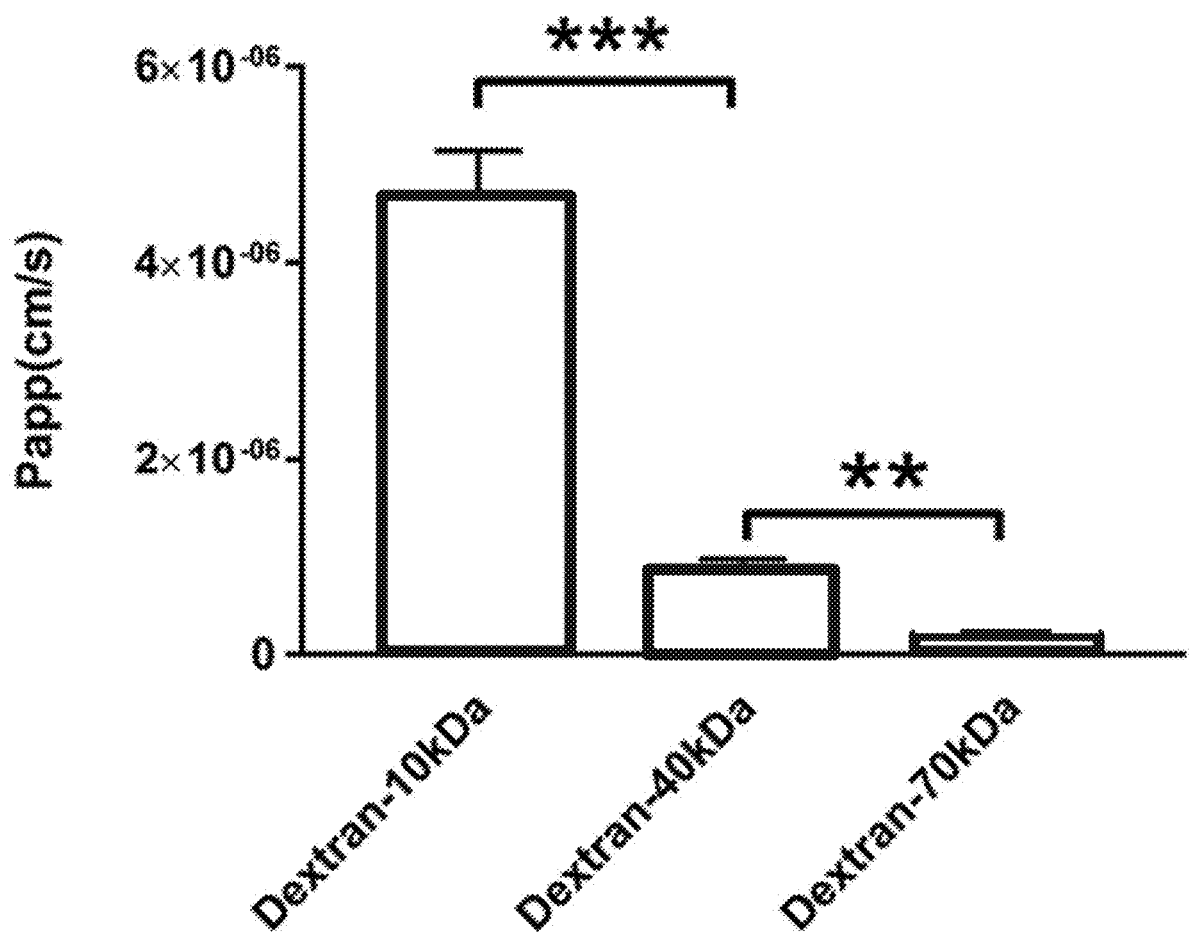
FIG. 7 depicts permeation rates of 3 Dextrans through endothelium with a glycocalyx in accordance with an example.

In another example, another method can include evaluating the density and integrity of the endothelial glycocalyx layer by measuring the permeation rates of Fluorescein Isothiocyanate Conjugate (FITC) Dextrans (FITC-Dextrans) at different molecular weights or sizes. Under normal physiological conditions, the endothelium can be selective to pass compounds based on their sizes, electrical charges, and the like. The endothelial selectivity can increase with a thick and health glycocalyx layer. The endothelial selectivity and barrier function can be compromised and lost when the endothelial glycocalyx is damaged or removed. The thickness and integrity of the endothelial glycocalyx can be evaluated and screened using endothelial glycocalyx protecting and regenerating compounds (eGPRC) by the determination of endothelial permeation of FITC-Dextrans of different sizes. As illustrated in FIG. 7, the permeation rates of three Dextrans through the endothelium of a healthy glycocalyx layer can be evaluated.

Example 3: Simulation of Pathological Condition for the Endothelial Glycocalyx

Figure 9:
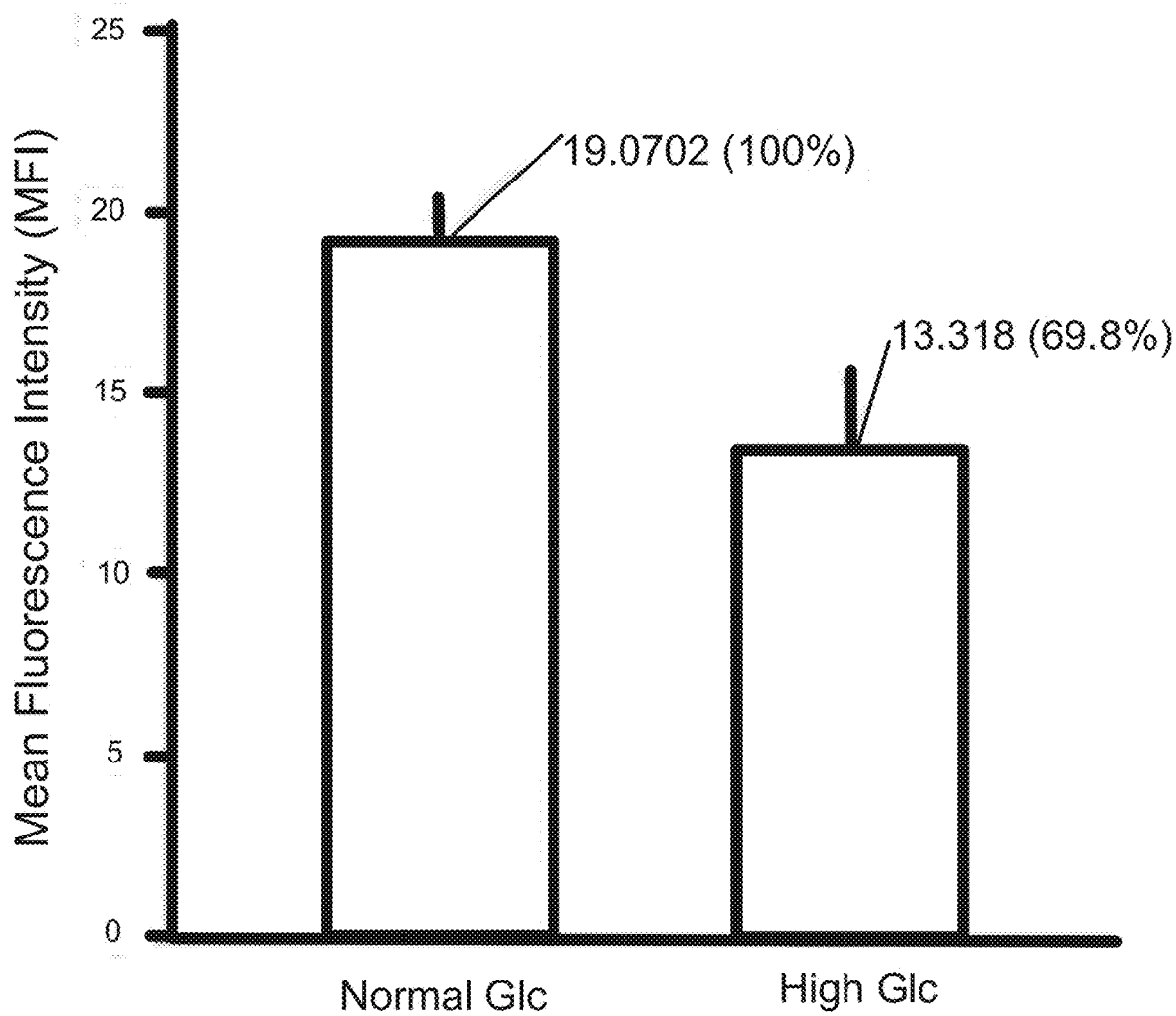
FIG. 9 depicts mean wheat germ agglutinin isothiocyanate conjugate (WGA-FITC) fluorescence intensity of the endothelial glycocalyx under a normal glucose condition and a high glucose condition in accordance with an example.
Figure 10A:
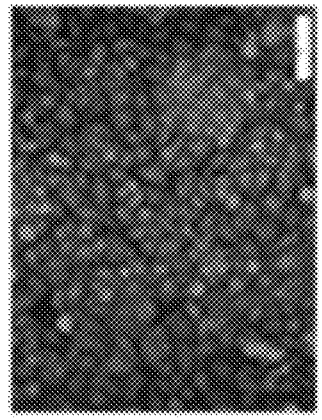
FIG. 10A-10I illustrates: human umbilical vein endothelial cells (HUVEC) morphology with a normal glucose level under a confocal microscope in accordance with an example (A); a nucleus with a normal glucose level under a confocal microscope in accordance with an example (B); glycocalyx with a normal glucose level under a confocal microscope in accordance with an example (C); HUVEC morphology with a high glucose level under a confocal microscope in accordance with an example (D); a nucleus with a high glucose level under a confocal microscope in accordance with an example (E); and glycocalyx with a high glucose level under a confocal microscope in accordance with an example (F); HUVEC morphology with a high glucose level in the presence of heparan sulfate under a confocal microscope in accordance with an example (G); a nucleus with a high glucose level in the presence of heparan sulfate under a confocal microscope in accordance with an example (H); and glycocalyx with a high glucose level in the presence of heparan sulfate under a confocal microscope in accordance with an example (I)
Figure 10B:
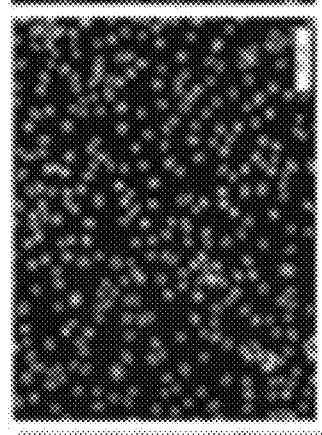
Figure 10C:
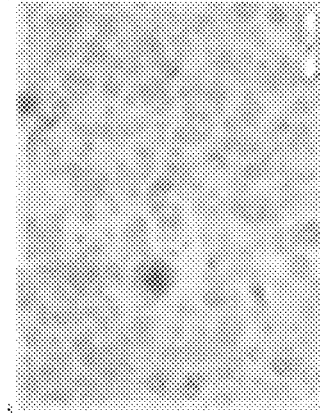
Figure 10D:
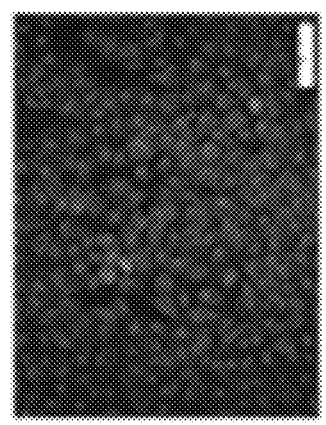
Figure 10E:
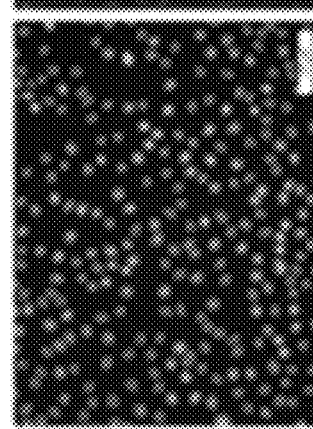
Figure 10F:
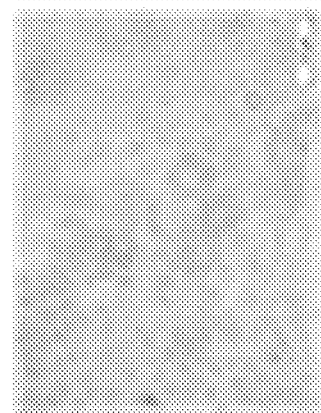
Figure 10G:
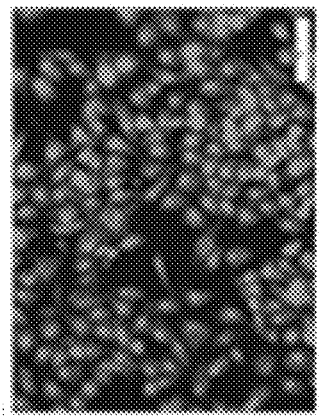
Figure 10H:
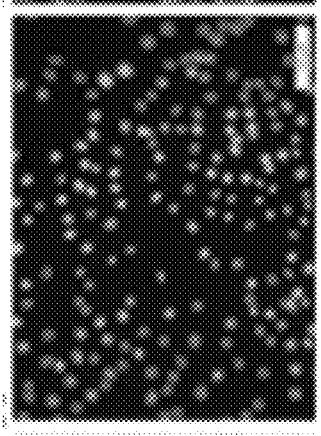
Figure 10I:
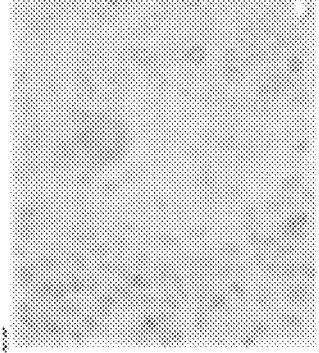

In another example, a method of simulating a pathological condition of the endothelial glycocalyx can include connecting the chip inlets (e.g., 116a, 116b, and 116c) to cell culture media with a glucose concentration range between 25-75 millimolar (mM) at the high flow rate (e.g., 250-300 μl/min in this case). The method of simulating the pathological condition of the endothelial glycocalyx can further include simulating hyperglycemic condition damage to the endothelial glycocalyx for 24-72 hours. The endothelial glycocalyx layer can be evaluated by WGA-FITC, as illustrated in FIG. 8, and FITC-Dextran permeation, as depicted in FIG. 9.

Example 4: Screening of Endothelial Glycocalyx Protecting and Regenerating Compounds (eGPGCs)

Figure 11:
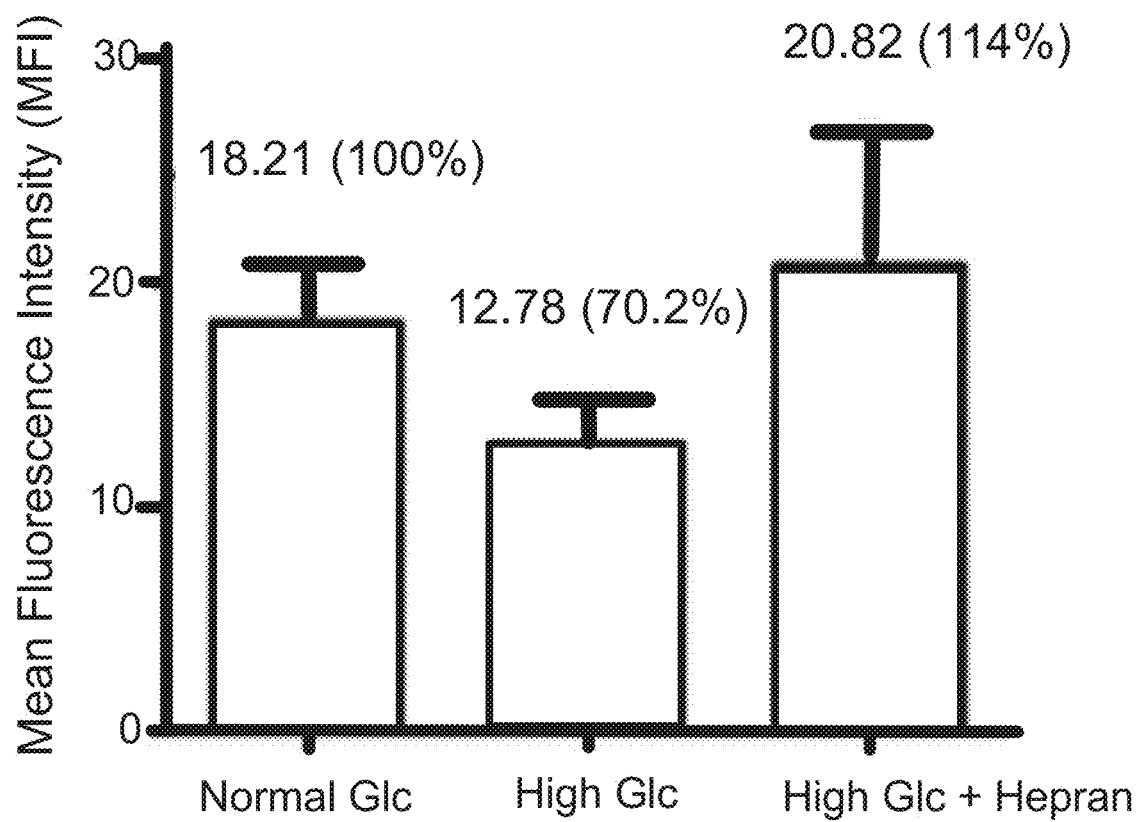
FIG. 11 depicts mean isothiocyanate conjugate (FITC) dextrans fluorescence intensity of the endothelial glycocalyx under a normal glucose condition, a high glucose condition, and a high glucose with heparan sulfate condition in accordance with an example.

In another example, as illustrated in FIG. 10, a method of screening GPRCs can include pumping cell culture media through both upper 114 and lower microchannels 112 in the microfluidic chip 100 at the same high flow rate (e.g., 250-300 μl/min in this case). The method of screening GPRCs can further include adding candidate endothelial glycocalyx protecting and regenerating compounds (eGPRCs) to the cell culture media with FITC-Dextrans under a pathological condition (i.e., hyperglycemic) for the upper microchannels 114. The method of screening GPRCs can further include, after 24 hours, collecting the cell culture media from the lower microchannels 112 and measuring their fluorescence intensity. The method of screening GPRCs can further include calculating permeation rates of different FITC-Dextrans (permeability coefficient (Papp) (centimeters (cm)/second(s))). As depicted in FIG. 11, the method of screening GPRCs can further include comparing the permeation rates of treatment groups with blank (normoglycemic), negative control (hyperglycemic) and positive control (with heparan sulfate) to determine whether the permeation rates have increased, decreased, or remain unchanged. The results can be used to determine whether a specific compound protects the endothelial glycocalyx.

In another example, HUVECs can be maintained with a high flow rate (e.g., 250-300 μl/min in this case) under a hyperglycemic condition for 24-72 hours. The cells can be perfused with a new cell culture medium with additional candidate eGPRCs under normoglycemic condition (regular glucose level in the cell culture medium) for different time periods. Afterwards, the cell culture media can be collected from the lower microchannels 112 and the fluorescence intensity of the cells can be measured. The permeation rates of different FITC-Dextrans (Papp (cm/s)) can be calculated. The permeation rates of treatment groups with blank (normoglycemic), negative control (hyperglycemic) and positive control (with heparan sulfate) can be compared to determine whether the permeation rates have increased, decreased, or remained unchanged. The foregoing results can be used to determine whether a specific compound contributes to the regeneration or restoration of the endothelial glycocalyx.

Example 5: Evaluate Glycocalyx Mediated Endothelial Functions in a Layer-by-Layer Microfluidic Chip In another example, using a layer-by-layer microfluidic chip, HUVEC cells can be seeded and grown on the surface of a porous biologically compatible membrane 113 in the upper microchannels 114. An appropriate cell culture medium can be pumped through the microchannels (i.e. cell culture chambers) at the high flow rates (e.g., 250-300 μl/min in this case) after 80% confluency. Different pathological conditions can be simulated by adding known components that damage the endothelial glycocalyx such as high levels of glucose to mimic hyperglycemic condition in diabetes. After 24-72 hours, microchannels can be perfused with human white blood cells in an appropriate cell culture medium at a physiologically relevant flow rate or flow stress. The interaction between white blood cells with endothelial cells such as monocyte adhesion can be visualized under a confocal microscope. Fluorescent-labeled human LDL and HDL can be added to the perforate. The LDL and HDL adhesion and penetration of the endothelial glycocalyx and endothelial cell layer can be visualized and measured. Lower cell culture chambers 112 can be maintained under the same conditions with the original cell culture media.

In another example, in different experiments, smooth muscle cells such as arterial smooth muscle cells from the human placenta can be seeded and grown in cell culture chambers of the lower layer 112 of a microfluidic chip 100. An appropriate cell culture medium can be pumped through the microchannels at the same low and appropriate flow rates to those on the top cell culture chambers 114. The changes of the endothelial glycocalyx can cause changes of endothelial permeation to different compounds such as LDL cholesterol. Endothelial cell layer can also undergo internal changes in response to the damage of endothelial glycocalyx. For example, the endothelial glycocalyx can act as a signal transducer for flow shear stress to trigger endothelial cells to synthesize nitric oxide (NO) via endothelial nitric oxide synthase (eNOS). NO can diffuse into smooth muscle cells to activate soluble guanylate cyclase (sGC) that can lead to smooth muscle relaxation in vivo. Morphological changes in smooth muscle cells can be observed under a confocal microscope. Smooth muscles cell can be harvested from microchannels for bioassays or lysed in situ. Changes in endothelial permeation on smooth muscle cell proteins including enzyme synthesis can be determined using fluorescence labeled monoclonal antibodies against the proteins. Changes in DNA or RNA expression in the smooth muscle cells can be quantified in the lower chamber.

Figure 12:
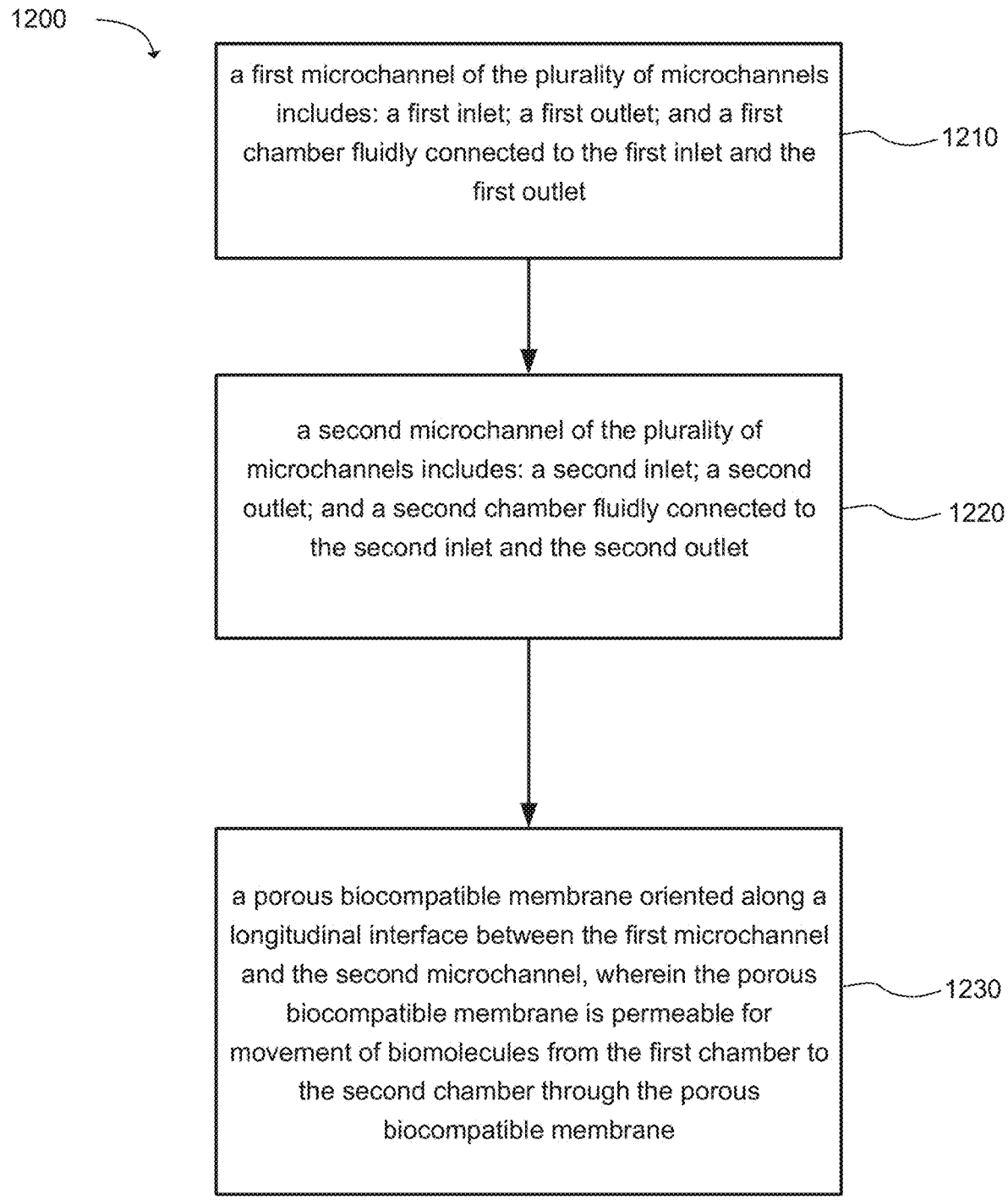
FIG. 12 depicts architecture of a microfluidic chip comprising a multichamber flow assembly in accordance with an example.

Another example provides a microfluidic chip comprising at least one multichamber flow assembly comprising a plurality of microchannels, as shown in FIG. 12. The microfluidic chip can comprise a first microchannel of the plurality of microchannels includes: a first inlet; a first outlet; and a first chamber fluidly connected to the first inlet and the first outlet, as in block 1210. The microfluidic chip can further comprise a second microchannel of the plurality of microchannels includes: a second inlet; a second outlet; and a second chamber fluidly connected to the second inlet and the second outlet, as in block 1220. The microfluidic chip can further comprise a porous biocompatible membrane oriented along a longitudinal interface between the first microchannel and the second microchannel, wherein the porous biocompatible membrane is permeable for movement of biomolecules from the first chamber to the second chamber through the porous biocompatible membrane, as in block 1230.

Figure 13:
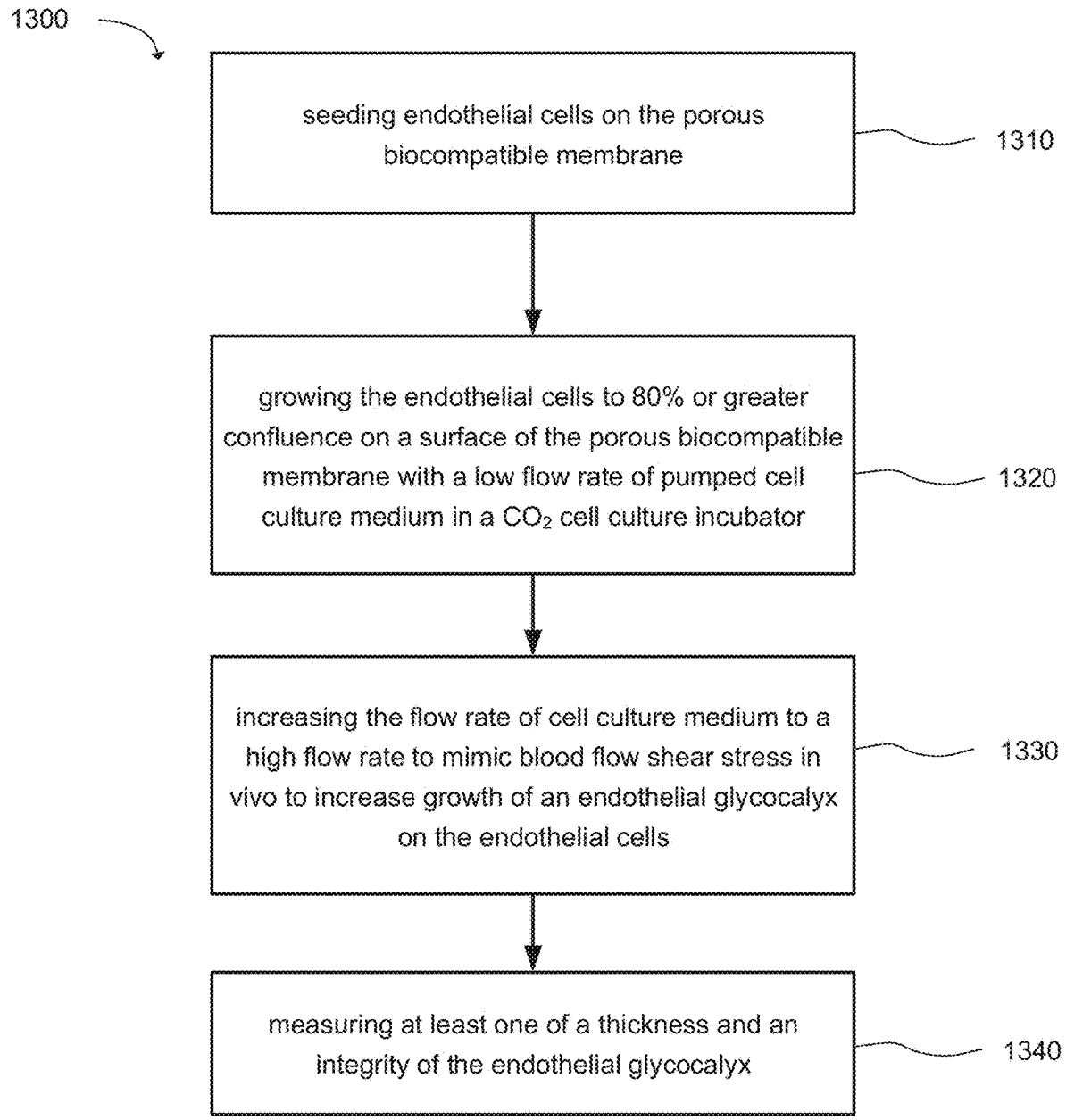
FIG. 13 depicts a method to grow endothelial cells with endothelial glycocalyx using a microfluidic chip in accordance with an example.

Another example provides a method to grow endothelial cells with endothelial glycocalyx using a microfluidic chip, as shown in FIG. 13. The method can comprise seeding endothelial cells on the porous biocompatible membrane, as in block 1310. The method can comprise growing the endothelial cells to 80% or greater confluence on a surface of the porous biocompatible membrane with a low flow rate of pumped cell culture medium in a $CO_2$ cell culture incubator, as in block 1320. The method can comprise increasing the flow rate of cell culture medium to a high flow rate to mimic blood flow shear stress in vivo to increase growth of an endothelial glycocalyx on the endothelial cells, as in block 1330. The method can comprise measuring at least one of a thickness and an integrity of the endothelial glycocalyx, as in block 1340.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A method to grow endothelial cells with endothelial glycocalyx using a microfluidic chip,
the microfluidic chip comprising:
at least one multichamber flow assembly comprising:
a plurality of microchannels, wherein:
a first microchannel of the plurality of microchannels includes:
a first inlet;
a first outlet; and
a first chamber fluidly connected to the first inlet and the first outlet; and
a second microchannel of the plurality of microchannels includes:
a second inlet;
a second outlet; and
a second chamber fluidly connected to the second inlet and the second outlet; and
a porous biocompatible membrane oriented along a longitudinal interface between the first microchannel and the second microchannel, wherein the porous biocompatible membrane is permeable for movement of biomolecules from the first chamber to the second chamber through the porous biocompatible membrane; and
the method comprising:
seeding endothelial cells on the porous biocompatible membrane;
growing the endothelial cells to 80% or greater confluence on a surface of the porous biocompatible membrane with a low flow rate of pumped cell culture medium in a $CO_2$ cell culture incubator;
increasing the flow rate of cell culture medium to a high flow rate to mimic blood flow shear stress in vivo to increase growth of an endothelial glycocalyx on the endothelial cells; and
measuring at least one of a thickness and an integrity of the endothelial glycocalyx, wherein the measuring is performed by at least one of:
a) a fluorescence intensity of wheat germ agglutinin fluorescein isothiocyanate conjugate (WGA-FITC) bound to the endothelial glycocalyx;
b) inserting glucose into the cell culture medium; maintaining the high flow rate to mimic a diabetic hyperglycemic condition; and measuring at least one of a stressed thickness and a stressed integrity of the endothelial glycocalyx; or
c) inserting at least one test compound with a test concentration into the cell culture medium; and measuring a test permeation rate related to at least one of a test thickness and a test integrity of the endothelial glycocalyx to measure at least one of protective impact and damage to the endothelial glycocalyx.

2. The method of claim 1, wherein the seeding is performed using a seeding medium having a cell density of $1 \times 10^4$ to $9 \times 10^6$ cells/milliliter (ml).

3. The method of claim 1, wherein:
the low flow rate is 1-60 microliters (µl)/minute (min);
the high flow rate is 250-300 µl/min; or
the high flow rate is selected to create a cell shear stress ranging between 10-23 dyne (dyn)/squared centimeter ($cm^2$).

4. The method of claim 1, further comprising:
perfusing the plurality of microchannels with a common cell culture medium at a medium flow rate ranging between 60-250 µl/min;
inserting a plurality of fluorescein isothiocyanate conjugate (FITC) DEXTRAN (FITC-DEXTRAN) with a plurality of sizes into the first microchannel for a first period of time;
measuring a fluorescence intensity in the second microchannel; and
calculating a permeation rate for each size of each FITC-DEXTRAN.

5. The method of claim 1, wherein the thickness and integrity of the endothelial glycocalyx is measured based on a permeation rate of a fluorescein isothiocyanate conjugate (FITC) DEXTRAN (FITC-DEXTRAN).

6. The method of claim 1, wherein the glucose is inserted at a concentration ranging between 25-75 millimolar (mM) and the high flow rate is maintained for a range between 24-72 hours.

7. The method of claim 1, further comprising:
inserting white blood cells into the cell culture medium to allow contact with the endothelial surface, wherein at least one of rolling on and adhesion to endothelial cell layers of white blood cells is determined using a confocal microscope.

8. The method of claim 1, wherein the endothelial cells are at least one of human umbilical vein endothelial cells, (HUVECs), human arterial endothelial cells (HAECs), bovine aortic endothelial cells (BAECs), pulmonary microvascular endothelial cells (PMVECs), pulmonary artery endothelial cells (PAECs), and human dermal microvascular endothelial cells (HDMECs).

9. The method of claim 1, further comprising:
growing smooth muscle cells in the second chamber; and
determining changes in at least one of RNA expression, DNA expression, and protein synthesis of the smooth muscle cells.

10. The method of claim 1, wherein the measuring is performed by only (a) of (a) through (c).

11. The method of claim 1, wherein the measuring is performed by only (b) of (a) through (c).

12. The method of claim 1, wherein the measuring is performed by only (c) of (a) through (c).

13. The method of claim 1, further comprising at least one of human umbilical endothelial cells (HUVECs), human arterial endothelial cells (HAECs), bovine aortic endothelial cells (BAECs), pulmonary microvascular endothelial cells (PMVECs), pulmonary artery endothelial cells (PAECs), and human dermal microvascular endothelial cells (HDMECs) adhered to the porous biocompatible membrane.

14. A method to grow endothelial cells with endothelial glycocalyx using a microfluidic chip,
the microfluidic chip comprising:
at least one multichamber flow assembly comprising:
a plurality of microchannels, wherein:
a first microchannel of the plurality of microchannels includes:
a first inlet;
a first outlet; and a first chamber fluidly connected to the first inlet and the first outlet; and a second microchannel of the plurality of microchannels includes:
- a second inlet;
- a second outlet; and
- a second chamber fluidly connected to the second inlet and the second outlet; and a porous biocompatible membrane oriented along a longitudinal interface between the first microchannel and the second microchannel, wherein the porous biocompatible membrane is permeable for movement of biomolecules from the first chamber to the second chamber through the porous biocompatible membrane; and the method comprising:
- seeding endothelial cells on the porous biocompatible membrane;
- growing the endothelial cells to 80% or greater confluence on a surface of the porous biocompatible membrane with a low flow rate of pumped cell culture medium in a $CO_2$ cell culture incubator;
- increasing the flow rate of cell culture medium to a high flow rate to mimic blood flow shear stress in vivo to increase growth of an endothelial glycocalyx on the endothelial cells;
- measuring at least one of a thickness and an integrity of the endothelial glycocalyx; and
- inserting white blood cells into the cell culture medium to allow contact with the endothelial surface, wherein at least one of rolling on and adhesion to endothelial cell layers of white blood cells is determined using a confocal microscope.

15. A method to grow endothelial cells with endothelial glycocalyx using a microfluidic chip, the microfluidic chip comprising:
- at least one multichamber flow assembly comprising:
  - a plurality of microchannels, wherein:
    - a first microchannel of the plurality of microchannels includes:
      - a first inlet;
      - a first outlet; and
      - a first chamber fluidly connected to the first inlet and the first outlet; and
    - a second microchannel of the plurality of microchannels includes:
      - a second inlet;
      - a second outlet; and
      - a second chamber fluidly connected to the second inlet and the second outlet; and
  - a porous biocompatible membrane oriented along a longitudinal interface between the first microchannel and the second microchannel, wherein the porous biocompatible membrane is permeable for movement of biomolecules from the first chamber to the second chamber through the porous biocompatible membrane; and the method comprising:
- seeding endothelial cells on the porous biocompatible membrane;
- growing the endothelial cells to 80% or greater confluence on a surface of the porous biocompatible membrane with a low flow rate of pumped cell culture medium in a $CO_2$ cell culture incubator;
- increasing the flow rate of cell culture medium to a high flow rate to mimic blood flow shear stress in vivo to increase growth of an endothelial glycocalyx on the endothelial cells;
- measuring at least one of a thickness and an integrity of the endothelial glycocalyx;
- growing smooth muscle cells in the second chamber; and
- determining changes in at least one of RNA expression, DNA expression, and protein synthesis of the smooth muscle cells.

* * * * *